(12) United States Patent
Dudley et al.

(10) Patent No.: US 8,034,334 B2
(45) Date of Patent: Oct. 11, 2011

(54) IMMUNOTHERAPY WITH IN VITRO-SELECTED ANTIGEN-SPECIFIC LYMPHOCYTES AFTER NON-MYELOABLATIVE LYMPHODEPLETING CHEMOTHERAPY

(75) Inventors: Mark E Dudley, Silver Spring, MD (US); Steven A Rosenberg, Potomac, MD (US); John R Wunderlich, Bethesda, MD (US)

(73) Assignee: The United States of America as represented by the Secretary, Department of Health and Human Services, Washington, DC (US)

( * ) Notice: Subject to any disclaimer, the term of this patent is extended or adjusted under 35 U.S.C. 154(b) by 836 days.

(21) Appl. No.: 10/526,697

(22) PCT Filed: Sep. 5, 2003

(86) PCT No.: PCT/US03/27873
§ 371 (c)(1),
(2), (4) Date: May 5, 2005

(87) PCT Pub. No.: WO2004/021995
PCT Pub. Date: Mar. 18, 2004

(65) Prior Publication Data
US 2006/0165652 A1 Jul. 27, 2006

Related U.S. Application Data

(60) Provisional application No. 60/408,681, filed on Sep. 6, 2002.

(51) Int. Cl.
*A01N 63/00* (2006.01)
*A61K 35/28* (2006.01)
*C12N 5/08* (2006.01)

(52) U.S. Cl. ............ 424/93.7; 424/577; 435/372.3

(58) Field of Classification Search ............ None
See application file for complete search history.

(56) References Cited

U.S. PATENT DOCUMENTS

| | | | |
|---|---|---|---|
| 4,690,915 A | 9/1987 | Rosenberg | |
| 5,126,132 A * | 6/1992 | Rosenberg | 424/85.2 |
| 5,192,537 A | 3/1993 | Osband | |
| 5,725,855 A | 3/1998 | Ochoa et al. | |
| 6,447,767 B1 | 9/2002 | Slavin et al. | |

FOREIGN PATENT DOCUMENTS

| | | | |
|---|---|---|---|
| WO | WO 97/05239 | * | 2/1997 |
| WO | WO 99/24045 A1 | | 5/1999 |
| WO | WO 03/004625 A1 | | 1/2003 |

OTHER PUBLICATIONS

Riddell et al J Immunol. Method, 1990, 128, pp. 189-201.*
Kawakami et al PNAS, 1994, V.91, pp. 6458-6462.*
Stevens et al., J. of Immunology, 1995, 154, pp. 762-771.*
Berenson et al., *J. Immunol.*, 115(1), 234-238 (1975).
Boehm et al., *Annu. Rev. Immunol.*, 15, 749-795 (1997).
Dudley et al., *J. Immunother.*, 24(4), 363-373 (2001).
Dudley et al., *J. Immunother.*, 25(3), 243-251 (2002).
Eberlein et al., *J. Exp. Med.*, 156(2), 385-397 (1982).
Luznik et al., *Blood*, 98(12), 3456-3464 (2001).
North, *J. Exp. Med.*, 55, 1063-1074 (1982).
O'Reilly et al., *Important Adv. Oncol.*, 149-166 (1996).
Robbins et al., *J. Immunol.*, 169, 6036-6047 (2002).
Rosenberg et al., *Ann. Surg.*, 228(3), 307-319 (1998).
Rosenberg et al., *J. Nat'l Cancer Inst.*, 86(15), 1159-1166 (1994).
Rosenberg et al., *Nat. Med.*, 4(3), 321-327 (1998).
Rosenberg et al., *Science*, 233, 1318-1321 (1986).
Seiter et al., *J. Immunother.*, 25(3), 252-263, (2002).
Yee et al., *J. Exp. Med.*, 192(11), 1637-1643 (2000).
EP Patent Application No. 03794636.5 Supplementary European Search Report dated Jan. 24, 2011.
Dudley, *Journal of Immunotherapy*, 22(4), 288-298 (Jul. 1, 1999).
Dudley, *Science, American Association for the Advancement of Science*, 298(5594), 805-854 (Oct. 25, 2002).
Overwijk et al., *The Cancer Journal from Scientific American (Online)*, Feb. 1-7, 2008, retrieved from the internet: URL:http://www.ncbi.nlm.nih.gov/pmc/articles/PMC2538796/pdf/nihms65816.pdf.
Rosenberg et al., *Journal of the National Cancer Institute*, 86(15), 1159-1166 (Aug. 3, 1994).

* cited by examiner

*Primary Examiner* — Michail Belyavskyi
(74) *Attorney, Agent, or Firm* — Leydig, Voit & Mayer

(57) ABSTRACT

A method of promoting the regression of a cancer in a mammal comprising: (i) administering to the mammal nonmyeloablative lymphodepleting chemotherapy, and (ii) subsequently administering: (a) autologous T-cells, which have been previously isolated, selected for highly avid recognition of an antigen of the cancer, the regression of which is to be promoted, and rapidly expanded in vitro only once, and, either concomitantly with the autologous T-cells or subsequently to the autologous T-cells, by the same route or a different route, a T-cell growth factor that promotes the growth and activation of the autologous T-cells, or (b) autologous T-cells, which have been previously isolated, selected for highly avid recognition of an antigen of the cancer, the regression of which is to be promoted, modified to express a T-cell growth factor that promotes the growth and activation of the autologous T-cells, and rapidly expanded in vitro only once, whereupon the regression of the cancer in the mammal is promoted.

18 Claims, No Drawings

SEQUENCE LISTING

<160> NUMBER OF SEQ ID NOS: 2

<210> SEQ ID NO 1
<211> LENGTH: 118
<212> TYPE: PRT
<213> ORGANISM: Homo sapiens

<400> SEQUENCE: 1

Met Pro Arg Glu Asp Ala His Phe Ile Tyr Gly Tyr Pro Lys Lys Gly
1               5                   10                  15

His Gly His Ser Tyr Thr Thr Ala Glu Glu Ala Ala Gly Ile Gly Ile
            20                  25                  30

Leu Thr Val Ile Leu Gly Val Leu Leu Leu Ile Gly Cys Trp Tyr Cys
        35                  40                  45

Arg Arg Arg Asn Gly Tyr Arg Ala Leu Met Asp Lys Ser Leu His Val
    50                  55                  60

Gly Thr Gln Cys Ala Leu Thr Arg Arg Cys Pro Gln Glu Gly Phe Asp
65                  70                  75                  80

His Arg Asp Ser Lys Val Ser Leu Gln Glu Lys Asn Cys Glu Pro Val
                85                  90                  95

Val Pro Asn Ala Pro Pro Ala Tyr Glu Lys Leu Ser Ala Glu Gln Ser
            100                 105                 110

Pro Pro Pro Tyr Ser Pro
        115

<210> SEQ ID NO 2
<211> LENGTH: 9
<212> TYPE: PRT
<213> ORGANISM: Artificial
<220> FEATURE:
<223> OTHER INFORMATION: Synthetic

<400> SEQUENCE: 2

Ile Met Asp Gln Val Pro Phe Ser Val
1               5

IMMUNOTHERAPY WITH IN VITRO-SELECTED ANTIGEN-SPECIFIC LYMPHOCYTES AFTER NON-MYELOABLATIVE LYMPHODEPLETING CHEMOTHERAPY

TECHNICAL FIELD OF THE INVENTION

The present invention relates to the combined use of immunotherapy and chemotherapy to promote the regression of a cancer in a mammal.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 5000 Byte ASCII (Text) file named "233876sequence.TXT," created on Nov. 6, 2007.

BACKGROUND OF THE INVENTION

The immunotherapy of patients with cancer requires the generation in vivo of large numbers of highly avid anti-tumor lymphocytes that can overcome normal tolerance and sustain an attack against a solid tumor. Immunization of melanoma patients with cancer antigens can increase the number of circulating CD8+ cytotoxic T-lymphocyte precursor cells (pCTL), but this has not correlated with clinical tumor regression, suggesting a defect in function or activation of the pCTL (Rosenberg et al., Nat. Med 4: 321 (1998)).

Adoptive cell transfer therapy provides the opportunity to overcome tolerogenic mechanisms by enabling the selection and ex vivo activation of highly selected T-cell subpopulations and by manipulating the host environment into which the T-cells are introduced. Prior clinical trials, including the transfer of highly active cloned anti-tumor T-cells failed to demonstrate engraftment and persistence of the transferred cells (Rosenberg et al., J. Nat'l. Cancer Inst. 86(15): 1159 (1994); Yee et al., J. Exp. Med. 192: 1637 (2000); Dudley et al., J. Immunother. 24(4): 363 (2001); Dudley et al., J. Immunother. 25(3): 243 (2002)). Lymphodepletion can have a marked effect on the efficacy of T-cell transfer therapy in murine models (Berenson et al., J. Immunol. 115: 234 (1975); Eberlein et al., J. Exp. Med. 156: 385 (1982); North, J. Exp. Med. 155: 1063 (1982); and Rosenberg et al., Science 233: 1318 (1986)) and may depend on the destruction of suppressor cells, disruption of homeostatic T-cell regulation, or abrogation of other normal tolerogenic mechanisms.

The present invention seeks to overcome the deficiencies in the art by providing a combined method of nonmyeloablative lymphodepleting chemotherapy and immunotherapy in which the transferred cells engraft and persist and promote the regression of a cancer. This and other objects and advantages of the present invention, as well as additional inventive features, will be apparent from the detailed description provided herein.

BRIEF SUMMARY OF THE INVENTION

The present invention provides a method of promoting the regression of a cancer in a mammal. The method comprises (i) administering to the mammal nonmyeloablative lymphodepleting chemotherapy and (ii) subsequently administering (a) autologous T-cells, which have been previously isolated, selected for highly avid recognition of an antigen of the cancer, the regression of which is to be promoted, and rapidly expanded in vitro only once, and, either concomitantly with the autolog us, T-cells or subsequently to the autologous T-cells, by the same route or a different route, a T-cell growth factor that promotes the growth and activation of the autologous T-cells, or (b) autologous T-cells, which have been previously isolated, selected for highly avid recognition of an antigen of the cancer, the regression of which is to be promoted, modified to express a T-cell growth factor that promotes the growth and activation of the autologous T-cells, and rapidly expanded in vitro only once, whereupon the regression of the cancer in the mammal is promoted.

Also provided is a method of promoting the regression of metastatic melanoma in a human. -The method comprises (i) intravenously administering around 60 mg/kg of cyclophosphamide for two days followed by around 25 mg/m$^2$ fludarabine for five days and (ii) subsequently intravenously administering (a) an infusion of around $2.3 \times 10^{10}$-$13.7 \times 10^{10}$ autologous T-cells, which have been previously isolated, selected for highly avid recognition of MART-1, and rapidly expanded in vitro only once, and, either concomitantly with the autologous T-cells or subsequently to the autologous T-cells, a bolus of about 720,000 IU/kg of IL-2 three times daily until tolerance, or (b) an infusion of around $2.3 \times 10^{10}$-$13.7 \times 10^{10}$ autologous T-cells, which have been previously isolated, selected for highly avid recognition of MART-1, modified to express IL-2, and rapidly expanded in vitro only once, whereupon the regression of the metastatic melanoma in the human is promoted.

Another method of promoting the regression of a cancer in a mammal is also provided. The method comprises (i) administering to the mammal nonmyeloablative lymphodepleting chemotherapy, and (ii) subsequently administering (a) autologous T-cells, which have been previously isolated, selected for highly avid recognition of an antigen of the cancer, the regression of which is to be promoted, by stimulation of the T-cells in vitro with the antigen of the cancer, and, optionally, rapidly expanded in vitro at least once by further stimulation with the antigen of the cancer, and, either concomitantly with the autologous T-cells or subsequently to the autologous T-cells, by the same route or a different route, a T-cell growth factor that promotes the growth and activation of the autologous T-cells, or (b) autologous T-cells, which have been previously isolated, selected for highly avid recognition of an antigen of the cancer, the regression of which is to be promoted, by stimulation of the T-cells in vitro with the antigen of the cancer, modified to express a T-cell growth factor that promotes the growth and activation of the autologous T-cells, and, optionally, rapidly expanded at least once in vitro by further stimulation with the antigen of the cancer, whereupon the regression of the cancer in the mammal is promoted.

DETAILED DESCRIPTION OF THE INVENTION

The present invention provides a method of promoting the regression of a cancer in a mammal. Desirably, the regression is complete, although one of ordinary skill in the art will appreciate that any degree of regression can be beneficial.

The method can be used to promote the regression of any cancer that expresses an antigen that can be recognized by in vitro-selected, autologous T-dells. Examples of such cancers include melanoma, lung carcinoma, breast cancer, colon cancer, prostate cancer, and the like. The method is particularly useful to promote the regression of melanoma, including metastatic melanoma, in a mammal.

The mammal can be any mammal. Preferably, the mammal is a human.

The method comprises (i) administering to the mammal nonmyeloablative lymphodepleting chemotherapy and (ii) (a) autologous T-cells, which have been previously isolated, selected for highly avid recognition of an antigen of the cancer, the regression of which is to be promoted, and rapidly expanded in vitro only once, and, either concomitantly with the autologous T-cells or subsequently to the autologous T-cells, by the same route or a different route, a T-cell growth factor that promotes the growth and activation of the autologous T-cells, or (b) autologous T-cells, which have been previously isolated, selected for highly avid recognition of an antigen of the cancer, the regression of which is to be promoted, modified to express a T-cell growth factor that promotes the growth and activation of the autologous T-cells, and rapidly expanded in vitro only once. The autologous T-cells can be heterogeneous, i.e., phenotypically diverse, e.g., include CD4+ T-cells among others, and/or can recognize more than one antigen of the cancer, such as two, three, four, or more antigens. The antigen(s) need not be unique to the cancer.

Alternatively, the method (referred to herein as "the alternative method") comprises (i) administering to the mammal nonmyeloablative lymphodepleting chemotherapy, and (ii) subsequently administering (a) autologous T-cells, which have been previously isolated, selected for highly avid recognition of an antigen of the cancer, the regression of which is to be promoted, by stimulation of the T-cells in vitro with the antigen of the cancer, and, optionally, rapidly expanded in vitro at least once by further stimulation with the antigen of the cancer, and, either concomitantly with the autologous T-cells or subsequently to the autologous T-cells, by the same route or a different route, a T-cell growth factor that promotes the growth and activation of the autologous T-cells, or (b) autologous T-cells, which have been previously isolated, selected for highly avid recognition of an antigen of the cancer, the regression of which is to be promoted, by stimulation of the T-cells in vitro with the antigen of the cancer, modified to express a T-cell growth factor that promotes the growth and activation of the autologous T-cells, and, optionally, rapidly expanded in vitro at least once by further stimulation with the antigen of the cancer, whereupon the regression of the cancer in the mammal is promoted. The autologous T-cells can be heterogeneous, i.e., phenotypically diverse, e.g., include CD4+ T-cells among others, and/or can recognize more than one antigen of the cancer, which need not be unique to the cancer, such as MART-1, in particular a peptide consisting of amino acids 26-35 of MART-1, in which amino acid 27 has been replaced with leucine, or gp100, in particular a peptide consisting of amino acids 209-217 of gp100, in which amino acid 210 has been replaced with methionine.

The nonmyeloablative lymphodepleting chemotherapy can be any suitable such therapy, which can be administered by any suitable route. The nonmyeloablative lymphodepleting chemotherapy can comprise the administration of cyclophosphamide and fludarabine, particularly if the cancer is melanoma, which can be metastatic. A preferred route of administering cyclophosphamide and fludarabine is intravenously. Likewise, any suitable dose of cyclophosphamide and fludarabine can be administered. Preferably, around 60 mg/kg of cyclophosphamide are administered for two days after which around 25 mg/m$^2$ fludarabine are administered for five days, particularly if the cancer is melanoma.

The autologous T-cells can be isolated from the mammal by any suitable means as are known in the art and exemplified herein in Examples 1 and 3. Similarly, selection methods for highly avid recognition of an antigen of the cancer, the regression of which is to be promoted, are known in the art and are exemplified herein in Examples 1 and 3. The autologous T-cells must be rapidly expanded in vitro only once, in accordance with methods known in the art and exemplified herein in Example 1, or, optionally, at least once (e.g., once, twice or thrice), in accordance with methods known in the art and exemplified herein in Example 3 (the alternative method). By "highly avid recognition" is meant HLA-restricted and antigen-specific recognition of an antigen of a cancer as evidenced, for example, by T-cell function, such as cytokine release or cytolysis.

Rapid expansion (as used herein, "rapid expansion" means an increase in the number of antigen-specific T-cells of at least about 3-fold (or 4-, 5-, 6-, 7-, 8-, or 9-fold) over a period of a week, more preferably at least about 10-fold (or 20-, 30-, 40-, 50-, 60-, 70-, 80-, or 90-fold) over a period of a week, or most preferably at least about 100-fold over a period of a week) of T-cell cultures can be accomplished by any of a number of methods as are known in the arts For example, the method of Example 1 utilizes non-specific T-cell receptor stimulation in the presence of feeder lymphocytes and either IL-2 or IL-15, with IL-2 being preferred. The non-specific T-cell receptor stimulus can consist of around 30 ng/ml of OKT3, a mouse monoclonal anti-CD3 antibody available from Ortho, Raritan, N.J.

The optional rapid expansion (as defined above) of T-cell cultures in accordance with the alternative method also can be accomplished by any of a number of methods as are known in the art. For example, the method of Example 3 involves stimulation of peripheral blood mononuclear cells (PBMC) in vitro with an antigen (one or more, including antigenic portions thereof, such as epitope(s), or a cell) of the cancer, which can be optionally expressed from a vector, such as an HLA-A2 binding peptide, e.g., 0.3 μM MART-1:26-35 (27L) or gp100: 209-217 (210M), in the presence of a T-cell growth factor, such as 300 IU/ml IL-2 or IL-15, with IL-2 being preferred. The in vitro-induced T-cells are rapidly expanded by re-stimulation with the same antigen(s) of the cancer pulsed onto HLA-A2-expressing antigen-presenting cells. Alternatively, the T-cells can be re-stimulated with irradiated, autologous lymphocytes or with irradiated HLA-A2+ allogeneic lymphocytes and IL-2, for example.

If the autologous T-cells are modified to express a T-cell growth factor that promotes the growth and activation of the autologous T-cells, any suitable methods of modification as are known in the art can be used. See, e.g., Sambrook and Russell, *Molecular Cloning*, 3$^{rd}$ ed., SCHL Press (2001). Desirably, modified autologous T-cells express the T-cell growth factor at high levels. T-cell growth factor coding sequences, such as that of IL-2, are readily available in the art, as are promoters, the operable linkage of which to a T-cell growth factor coding sequence promote high-level expression.

T-cells can be selected for highly avid recognition of any of the unique antigens produced as a result of the estimated 10,000 genetic mutations encoded by each tumor cell genome. The antigen, however, need not be unique. T-cells can be selected for highly avid recognition of one or more antigens of a cancer, including an antigenic portion of one or more antigens, such as an epitope, or a cell of the cancer. An "antigen of a cancer" and an "antigen of the cancer" are intended to encompass all of the aforementioned antigens. If the cancer is melanoma, such as metastatic melanoma, preferably the T-cells are selected for highly avid recognition of MART-1 (such as MART-1:26-35 (27L)), gp100 (such as gp100:209-217 (210M)), or a "unique" or patient-specific antigen derived from a tumor-encoded mutation. Other suitable melanoma antigens for which highly avid recognition by T-cells can be selected include, but are not limited to, tyrosinase, tyrosinase related protein (TRP)1, TRP2, and MAGE. Antigens, such as NY-ESO-1, telomerase, p53, HER2/neu, carcinoembryonic antigen, or prostate-specific antigen, can be used to select for highly avid recognition by T-cells for treatment of lung carcinoma, breast cancer, colon cancer, prostate cancer, and the like.

The T-cells can be administered by any suitable route as known in the art. Preferably, the T-cells are administered as an intra-arterial or intravenous infusion, which preferably lasts approximately 30-60 min. Other examples of routes of administration include intraperitoneal, intrathecal and intra-lymphatic.

Likewise, any suitable dose of T-cells can be administered. Preferably, from about $2.3 \times 10^{10}$ T-cells to about $13.7 \times 10^{10}$ T-cells are administered, with an average of around $7.8 \times 10^{10}$ T-cells, particularly if the cancer is melanoma. With respect to the alternative method, preferably, from about $1.2 \times 10^{10}$ to about $4.3 \times 10^{10}$ T-cells are administered.

The T-cell growth factor can be any suitable growth factor that promotes the growth and activation of the autologous T-cells administered. Examples of suitable T-cell growth factors include IL-2, IL-7 and IL-15, which can be used alone or in various combinations, such as IL-2 and IL-7, IL-2 and IL-15, IL-7 and IL-15, or IL-2, IL-7 and IL-15. IL-2 is a preferred T-cell growth factor. A preferred source for IL-2 is Chiron, Emerwlle, Calif., whereas a preferred source for IL-7 is Cytheris, Vanves, Frances. IL-15 can be obtained from PeproTech, Inc., Rocky Hill, N.J.

Studies with mice into which B16 murine melanoma cells had been subcutaneously injected and which, after 12 days, had been irradiated with a sublethal dose (500 rads) of radiation and injected with tumor-specific T-cells (Pmel, derived from T-cell transgenic mouse), fowlpox virus human gp100, and either IL-2, IL-7 and/or IL-15 indicated that IL-2, IL-7 and IL-15 individually delay tumor growth about the same. Similarly, IL-2 and IL-7, IL-2 and IL-15, and IL-7 and IL-15 delay tumor growth about the same. However, two cytokines are more effective than a single cytokine and three cytokines, e.g., IL-2, IL-7 and IL-15, are better than any two cytokines. Preliminary data suggest that IL-15 enhances a tumor-specific CD8+ T-cell response. In this regard, the administration of IL-15-cultured cells with IL-2 (such as a bolus injection) can be particularly efficacious.

The T-cell growth factor can be administered by any suitable route. If more than one T-cell growth factor is administered, they can be administered simultaneously or sequentially, in any order, and by the same route or different routes. Preferably, the T-cell growth factor, such as IL-2, is administered intravenously as a bolus injection. Desirably, the dosage of the T-cell growth factor, such as IL-2, is what is considered by those of ordinary skill in the art to be high. Preferably, a dose of about 720,000 IU/kg of IL-2 is administered three times daily until tolerance, particularly when the cancer is melanoma Preferably, about 5 to about 12 doses of IL-2 are administered, with an average of around 9 doses.

In view of the foregoing, the present invention provides a method of promoting the regression of metastatic melanoma in a human. The method comprises (i) intravenously administering around 60 mg/kg of cyclophosphamide for two days followed by around 25 mg/m² fludarabine for five days and (ii) subsequently intravenously administering (a) an infusion of around $2.3 \times 10^{10}$-$13.7 \times 10^{10}$ autologous T-cells, which have been previously isolated, selected for highly avid recognition of MART-1, and rapidly expanded in vitro only once, and, either concomitantly with the autologous T-cells or subsequently to the autologous T-cells, a bolus of about 720,000 IU/kg of IL-2 three times daily until tolerance, or (b) an infusion of around $2.3 \times 10^{10}$-$13.7 \times 10^{10}$ autologous T-cells, which have been previously isolated, selected for highly avid recognition of MART-1, modified to express IL-2, and rapidly expanded in vitro only once, whereupon the regression of the metastatic melanoma in the human is promoted. Preferably, around $7.8 \times 10^{10}$ T-cells are administered. Preferably, from about 5 to about 12 doses of IL-2 are administered, with an average of around 9 doses. Preferably, the intravenous infusion lasts approximately 30-60 min.

The above method can be adapted to immunodeficiency diseases and autoimmune diseases, such as AIDS, as well as infectious diseases, such as infection with human immunodeficiency virus (HIV).

EXAMPLES

The following examples serve to illustrate the present invention and are not intended to limit its scope in any way.

Example 1

This example describes the effect of prior lymphodepletion on the persistence and function of adoptively transferred cells.

Thirteen HLA-A2 positive patients with metastatic melanoma received immunodepleting chemotherapy with cyclophosphamide (60 mg/kg) for two days followed by fludarabine (25 mg/m²) for five days. On the day following the final dose of fludarabine, when circulating lymphocytes and neutrophils had dropped to less than 20/mm³, rapidly expanded, highly selected, autologous, tumor-reactive (IFN-γ release of greater than 100 pg/ml and at least two times greater than control when stimulated with an HLA-A2-matched melanoma or an autologous melanoma cell line) T-cell cultures (derived from tumor-infiltrating lymphocytes (TIL) obtained by plating $1 \times 10^6$ viable cells of a single-cell suspension of enzymatically digested explant of metastatic melanoma into 2 ml of medium containing 6,000 IU/ml of IL-2 (Rosenberg et al. (1994), supra; Dudley et al. (2002), supra) and maintained at $5 \times 10^5$-$2 \times 10^6$ cells/ml until several million T-cells, then screened for tumor cell recognition by cytokine secretion, most active cultures further expanded in IL-2 to a total cell number above $1 \times 10^8$; followed by one cycle of rapid expansion, using irradiated allogeneic feeder cells, OKT3 antibody and IL-2 (Riddell et al., J. Immunol. Methods 128: 189 (1990)), prior to use) were harvested and pooled for patient intravenous infusion (average of $7.8 \times 10^{10}$ cells; range of 2.3-$13.7 \times 10^{10}$ cells) over approximately 30-60 min and high-dose IL-2 therapy (720,000 IU/kg by bolus intravenous infusion every eight hours to tolerance; average of 9 doses; range of 5-12 doses). All patients had progressive disease refractory to standard therapies, including high-dose IL-2, and eight patients also had progressed through aggressive chemotherapy.

Response was assessed by radiographic measurements and physical examination. A complete response was defined as the complete disappearance of all evaluable disease. A partial response was defined as a decrease equal to or greater than 50% in the sum of the products of perpendicular diameters of all lesions without the growth of any lesion or the appearance of any new lesion. A mixed response was defined as a decrease in the area of some lesions with concurrent growth of other lesions or the appearance of new lesions. Six of the 13 patients had objective clinical responses to treatment and four others demonstrated mixed responses with significant shrinkage of one or more metastatic deposits. Objective tumor regression was seen in the lung, liver, lymph nodes, and intraperitoneal masses, and at cutaneous and subcutaneous sites. Five patients, all with evidence of concomitant cancer regression, demonstrated signs of autoimmune melanocyte destruction. All patients recovered from treatment with absolute neutrophil counts greater than 500/mm$^3$ by day 11, but slower recovery of CD4 cells as expected following fludarabine therapy (Cheson, J. Clin. Oncol. 13: 2431 (1995)). One patient had a transient respiratory syncytial virus pneumonia during treatment that cleared within one week.

Example 2

This example describes the function and fate of the adoptively transferred T-cells.

T-cell receptor (TCR) expression was examined in the six patients for whom peripheral blood samples were available at one week and approximately one month post-cell transfer, using two-color FACS with an FITC-conjugated CD8-specific antibody and a panel of PE-conjugated β-chain variable region (Vβ)-specific antibodies. Vβ expression was highly skewed in five of the six administered TIL, and these same Vβ families were also over-represented in the peripheral blood of the patients at one week after cell transfer. Two patients exhibited prolonged persistence of individual T-cell receptor Vβ families that predominated the T-cell repertoire. Within a few days of cessation of IL-2 therapy following TIL transfer, these two patients exhibited a pronounced lymphocytosis, with one patient having an absolute lymphocytic count (ALC) reaching peak levels in peripheral blood of over 21,000 cells/mm$^3$ on day 7 post-cell infusion, and the other patient having an ALC reaching peak levels in peripheral blood of over 16,000 cells/mm$^3$ on day 8 post-cell infusion. Only a few Vβ families dominated the T-cell repertoire of the peripheral blood when analyzed with the antibody panel. Peripheral blood lymphocytes (PBLs) from one patient (ALC of 21,000 cells/mm$^3$) sampled at the peak of the lymphocytosis were 94% CD8+, of which 63% expressed Vβ12. Even more pronounced skewing of the T-cell repertoire was observed in the peripheral blood of the other patient (ALC of 16,000 cells/mm$^3$) sampled at the peak of lymphocytosis, when 96% of the lymphocytes were CD8+, of which 97% expressed Vβ7.

Additional analysis of TCR usage in PBLs was undertaken using RT-PCR with PCR primers that were designed to amplify all Vβ gene families (McKee et al., J. Immunother. 23: 419 (2000)). Seven days after cell transfer, strong RT-PCR products were seen in PBL from one patient (ALC of 21,000 cells/mm$^3$) for the reactions with Vβ12 and Vβ14 primers and faint bands from reactions with Vβ4, Vβ6 and Vβ13 primers. PBL from the other patient (ALC of 16,000 cells/mm$^3$) eight days after TIL transfer demonstrated a strong product only in the reaction using the Vβ7 primers. Thus, at the RNA and protein levels, individual TCR Vβ families constituted a majority of the lymphocytes from peripheral blood of both patients one week after TIL transfer.

In order to assess the diversity of the TCR within the over-expressed Vβ families, the nucleotide sequence of the β-chain V-D-J regions was determined. The Vβ12-specific RT-PCR products from one patient (ALC of 21,000 cells/mm$^3$) were cloned, and six clones each from PBL and TIL were found to have identical sequence and to be identical to the V-D-J sequence from MART-1-reactive T-cell clone derived from the TIL. MART-1 is a normal, non-mutated differentiation antigen expressed on melanomas and normal melanocytes (Kawakami et al., PNAS USA 91: 3515 (1994)).

The sequence of the Vβ7-specific RT-PCR products from the other patient (ALC of 16,000 cells/mm$^3$) also had identical V-D-J sequences, whether derived from PBL, TIL or a MART-1-reactive T-cell clone derived from the TIL. These results demonstrate that clonal, MART-1-reactive, T-cell populations within the TIL infused into these two patients repopulated the immune systems of these patients. Furthermore, these results suggested that the individual clones underwent large numerical expansion in vivo. Assuming an average blood volume of 4 liters, one patient (ALC of 21,000 cells/mm$^3$) had more than $5.0 \times 10^{10}$ circulating Vβ12 lymphocytes, while he was infused with only approximately $1.2 \times 10^{10}$ Vβ12 TIL. The other patient (ALC of 16,000 cells/mm$^3$) had at least $5.6 \times 10^{10}$ circulating Vβ7 lymphocytes, while he was infused with $9.5 \times 10^{10}$ Vβ7 TIL. Even without accounting for additional cells within lymphoid tissues or infiltrating into solid tissues, the preponderance of only a single clone in the peripheral blood of these two patients during their lymphocytic episodes was striking.

The MART-1 reactive clones predominated the CD8+ PBL of these two patients for over four months. The lymphocytosis resolved and white blood cell counts returned to homeostatic levels over the course of several weeks. As measured by Vβ12 antibody and by A2/MART-1 tetramer FACS analysis, the MART-1 reactive clone in the patient with an ALC of 21,000 cells/mm$^3$ remained above 60% of the CD8+ lymphocytes for over 123 days. The patient with an ALC of 16,000 cells/mm$^3$ retained the MART-1 reactive Vβ7 T-cell at more than 75% of the CD8+ cells for over 159 days from the date of transfer.

The functional status of the MART-1-reactive cells was tested after transfer by comparing the lytic activity of the PBL during the peak of lymphocytosis with PBL prior to infusion and with the infused TIL by cell-mediated lympholysis assay. High levels of specific lysis of MART-1:27-35 peptide pulsed targets and MART-1-expressing HLA-A2+ tumor cell lines were observed in the infused TIL and the post-infusion PBL. Blood smears of PBL from both patients demonstrated that the circulating lymphocytes exhibited an atypical, blastic and highly active morphology, consistent with their direct ex vivo lytic function. Additionally, PBL from both patients secreted little or no inflammatory cytokines when stimulated by tumor cell lines; however, overnight activation of post-transfer PBL in IL-2 restored the specific secretion of inflammatory cytokines, including IFN-γ, GM-CSF and TNF-α. These results suggest that the persistent cells may be in an intermediate state of activation, and that appropriate activation signals at the tumor site in situ could induce antigen-specific proinflammatory cytokine secretion as well as lytic activity from the persistent T-cell clones.

The ability of transferred cells to traffic to tumor deposits was investigated by analysis of tumor specimens from the two patients obtained by excisional biopsy before treatment and at multiple times after treatment. After treatment, the biopsied specimens contained large areas of necrotic tumor, and areas of dense, diffuse lymphocytic infiltrates. Immunohistochemical staining revealed that the lymphocytic infiltrates consisted predominantly of CD8+ cells. The infiltrating T-cells from the patient with an ALC of 21,000 cells/mm$^3$ were predominantly Vβ12, but not Vβ7, while T-cells infiltrating tumor tissue from the patient with an ALC of 16,000 cells/mm$^3$ were predominantly Vβ7, but not Vβ12. RNA from the biopsied specimens of the patient with an ALC of 21,000 cells/mm$^3$ obtained 20 days after cell transfer was analyzed by RT-PCR using the panel of Vβ-specific primers and Vβ12 was a predominant product in two independent tumor specimens (Vβ14 was not evident in either sample). Sequence analysis of the Vβ12 V-D-J region from tumor tissue revealed that the β-chain sequence was identical to the Vβ12-derived sequence of the TIL, the post-treatment PBL, and the MART-1-specific clone. Both of MHC class I and MHC class II antigens were highly expressed in tumor deposits after therapy, but expressed only at low levels or not at all in tumors prior to TIL treatment. MHC class I and class II antigen expression in tumor cells is indicative of an ongoing inflammatory immune reaction, and IFN-γ is known to induce the expression of these antigens (Boehm et al., Ann. Rev. Immunol. 15: 749 (1997)). Taken together, these results are consistent with trafficking to the tumor of the in vivo-expanded Vβ12 (patient with ALC of 21,000 cells/mm$^3$) or Vβ7 (patient with ALC of 16,000 cells/mm$^3$) TIL, recognition of the MART-1 antigen of the tumor cells, secretion of IFN-γ and other cytokines by the activated lymphocytes, and establishment of an inflammatory anti-tumor immune response within the tumor nodules.

Both patients exhibited significant regression of metastatic melanoma and the onset of anti-melanocyte auto-immunity. One patient (ALC of 21,000 cells/mm$^3$) exhibited regression of more than 95% of his cutaneous and subcutaneous melanoma, and developed vitiligo on his forearms. His metastatic melanoma has shown no sign of recurrence at eight months after treatment. At four months after cell infusion, he developed an EBV-related lympho-proliferative disease (he was EBV sero-negative prior to treatment) that has been reported in EBV sero-negative patients receiving allogeneic transplants (O'Reilly et al., Important Adv. Oncol. 149 (1996)) and is undergoing treatment for this problem. The other patient (ALC of 16,000 cells/mm$^3$) exhibited 99% disappearance of his nodal, cutaneous and subcutaneous melanoma Fourteen days after cell infusion, during the active regression of melanoma, he developed bilateral acute anterior uveitis characterized by a fibrinous pupillary membrane. This autoimmune manifestation had not been detected in over 600 patients who were treated with high dose IL-2, including many who exhibited objective clinical response to treatment (Rosenberg et al., Ann. Surg. 228: 307 (1998)). He has responded to steroid eye drops to suppress inflammation, and remains healthy with normal vision and without signs of recurrent melanoma over seven months after treatment. Although the absolute lymphocyte counts decayed to normal levels after 3-4 weeks in both patients, the composition of the resulting lymphocyte pool remained highly skewed.

Example 3

This example describes the effect of prior lymphodepletion on the persistence and function of adoptively transferred cells.

Two HLA-A2 positive patients with metastatic melanoma received immunodepleting chemotherapy with cyclophosphamide (60 mg/kg) for two days followed by fludarabine (25 mg/m$^2$) for five days. On the day following the final dose of fludarabine, when circulating lymphocytes and neutrophils had dropped to less than 20/mm$^3$, in vitro-induced, autologous, tumor-reactive (IFN-γ release of greater than 100 pg/ml and at least two times greater than control when stimulated with an HLA-A2-matched melanoma or an autologous melanoma cell line) T-cell cultures (derived from peripheral blood mononuclear cells (PBMC) obtained by in vitro culture of multiple flasks, each containing 6×10$^7$ viable cells of a ficoll-hypaque enriched lymphopheresis with 0.3 µM MART-1:26-35(27L) peptide or 0.3 µM gp100:209-217(210M) peptide in 100 ml of medium containing 300 IU/ml of IL-2 and maintained at 5×10$^5$-2×10$^6$ cells/ml for 11 days; followed by one cycle of peptide-mediated rapid expansion; using irradiated autologous PBMC pulsed with 1.0 µM of MART-1:26-35 (27L) peptide or 1.0 µM of gp100:209-217(210M) peptide and IL-2), were harvested and pooled for patient intravenous infusion (patient 1 received 1.2×10$^{10}$ cells; patient 2 received 4.3×10$^{10}$ cells) over approximately 30-60 min and high-dose IL-2 therapy (720,000 IU/kg by bolus intravenous infusion every eight hours to tolerance). Both patients had progressive disease refractory to standard therapies, including high-dose IL-2, and aggressive chemotherapy.

One patient exhibited a mixed response including a partial response of her lung disease, with a decrease in hundreds of lung metastatic deposits equal to or greater than 50% in the sum of the products of perpendicular diameters of all measured lesions without the growth of any lesion or the appearance of any new lesion. The other patient exhibited a stable disease that is ongoing with a decrease of less than 50% in the area of all her subcutaneous lesions. One patient also demonstrated vitiligo, or autoimmune destruction of skin melanocytes. Neither patient exhibited any unexpected adverse reaction attributable to the treatment. Both patients demonstrated the persistence in the peripheral blood of high levels of antigen-specific T cells after treatment, as measured by A2/gp100 or A2/MART-1 tetramer FACS analysis, consistent with the successful immune repopulation with tumor antigen-reactive T cells.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of promoting the regression of a cancer in a mammal, which method comprises:
   (i) administering to the mammal nonmyeloablative lymphodepleting chemotherapy, and
   (ii) subsequently administering:
      (a) autologous T-cells, which have been previously isolated, and selected for highly avid recognition of an antigen of the cancer, the regression of which is to be promoted, by stimulation of the T-cells in vitro with the antigen of the cancer, followed by one cycle of rapid expansion using irradiated allogeneic feeder cells, OKT3 antibody, and IL-2, and, either concomitantly with the autologous T-cells or subsequently to the autologous T-cells, by the same route or a different route, a T-cell growth factor that promotes the growth and activation of the autologous T-cells, or
      (b) autologous T-cells, which have been previously isolated, selected for highly avid recognition of an antigen of the cancer, the regression of which is to be promoted, by stimulation of the T-cells in vitro with the antigen of the cancer, and modified to express a T-cell growth factor that promotes the growth and activation of the autologous T-cells, followed by one cycle of rapid expansion using irradiated allogeneic feeder cells, OKT3 antibody, and IL-2 whereupon the regression of the cancer in the mammal is promoted.

2. The method of claim 1, wherein the T-cell growth factor is IL-2, IL-7, IL-15, or a combination of two or all of the foregoing.

3. The method of claim 1, wherein the nonmyeloablative lymphodepleting chemotherapy comprises the administration of cyclophosphamide and fludarabine.

4. The method of claim 3, wherein around 60 mg/kg of cyclophosphamide are administered for two days after which around 25 mg/m$^2$ fludarabine are administered for five days.

5. The method of claim 4, wherein the cyclophosphamide and fludarabine are administered intravenously.

6. The method of claim 2, wherein a dose of about 720,000 IU/kg of IL-2 is administered three times daily until tolerance.

7. The method of claim 6, wherein from about 5 to about 12 doses of IL-2 are administered.

8. The method of claim 7, wherein around 9 doses of IL-2 are administered.

9. The method of claim 6, wherein the dose of IL-2 is administered as a bolus intravenous injection.

10. The method of claim 1, wherein from about $1.2 \times 10^{10}$ T-cells to about $4.3 \times 10^{10}$ T-cells are administered.

11. The method of claim 1, wherein the T-cells are administered as an intravenous infusion.

12. The method of claim 11, wherein the intravenous infusion lasts approximately 30-60 min.

13. The method of claim 1, wherein the cancer is melanoma.

14. The method of claim 13, wherein the T-cells bind to MART-1 (SEQ ID NO: 1).

15. The method of claim 1, wherein the cancer is metastatic.

16. The method of claim 1, wherein the mammal is a human.

17. The method of claim 1, wherein the antigen of the cancer consists of amino acids 26-35 of MART-1 (SEQ ID NO: 1), in which amino acid 27 has been replaced with leucine.

18. The method of claim 1, wherein the antigen of the cancer is the gp100:209-217 (210M) peptide (SEQ ID NO: 2).

* * * * *